United States Patent [19]

Lindström

[11] Patent Number: 5,618,671
[45] Date of Patent: Apr. 8, 1997

[54] METHOD AND SYSTEM FOR MOLECULAR-BIOLOGICAL DIAGNOSTICS

[75] Inventor: Per Lindström, Uppsala, Sweden

[73] Assignee: Pharmacia Biotech AB, Uppsala, Sweden

[21] Appl. No.: 356,346

[22] PCT Filed: Jun. 23, 1993

[86] PCT No.: PCT/SE93/00557

§ 371 Date: Dec. 22, 1994

§ 102(e) Date: Dec. 22, 1994

[87] PCT Pub. No.: WO94/00597

PCT Pub. Date: Jan. 6, 1994

[30] Foreign Application Priority Data

Jun. 23, 1992 [SE] Sweden ................................ 9201929

[51] Int. Cl.$^6$ .............................. C12P 19/34; C12Q 1/00; C12Q 1/68
[52] U.S. Cl. ........................... 435/6; 435/91.1; 435/91.2; 435/285.1; 435/287.2; 436/501
[58] Field of Search ................. 435/6, 91.1, 91.2, 435/287, 289, 290, 291; 436/501; 935/77, 78

[56] References Cited

U.S. PATENT DOCUMENTS

| | | | |
|---|---|---|---|
| 4,707,235 | 11/1987 | Englert et al. | 204/182.8 |
| 4,891,319 | 1/1990 | Roser | 435/188 |
| 4,988,617 | 1/1991 | Landegren et al. | 435/6 |
| 4,998,617 | 3/1991 | Ladd, Jr. et al. | 206/219 |
| 5,098,893 | 3/1992 | Franks et al. | 514/54 |
| 5,382,511 | 1/1995 | Stapleton | 435/6 |

FOREIGN PATENT DOCUMENTS

| | | |
|---|---|---|
| 0298669 | 1/1989 | European Pat. Off. . |
| 0326989 | 8/1989 | European Pat. Off. . |
| WO/9009455 | 8/1990 | WIPO . |
| WO/9108308 | 6/1991 | WIPO . |
| WO/9202303 | 2/1992 | WIPO . |
| WO/9411529 | 5/1994 | WIPO . |

OTHER PUBLICATIONS

WO 91/09964 International Publication Date: 11 Jul. 1991.
WO 89/10977 International Publication Date: 16 Nov. 1989.
WO 88/03572 International Publication Date: 19 May 1988.
WO 88/06633 International Publication Date: 7 Sep. 1988.
Syvänen et al. International Journal of Cancer (1992, Mar.) 50(5):713–718.

*Primary Examiner*—Stephanie W. Zitomer
*Assistant Examiner*—Paul B. Tran
*Attorney, Agent, or Firm*—Birch, Stewart, Kolasch & Birch, LLP

[57] ABSTRACT

In a method for molecular-biological analysis of genetic material, a genomic DNA or RNA preparation is tested for the presence of mutations. The processed DNA or RNA preparation is contacted with a first set(s) of interconnected solid phase members (5) supporting oligonucleotide primers to bind a defined DNA or RNA fragment that may contain a stable mutation to each solid phase member, and/or with a second set(s) of interconnected solid phase members (5) supporting oligonucleotide primers to bind a defined DNA or RNA fragment that may contain an unstable mutation or several stable mutations to each solid phase member. The solid phase members (5) of the first set(s) are introduced into a matching first set(s) of interconnected receptacles (7) with reaction mixtures for producing products which contain an incorporated marker when a supported DNA or RNA fragment has a mutation. The solid phase members (5) of the second set(s) are introduced into a matching second set(s) of interconnected receptacles (7) containing reaction mixtures for performing sequencing reactions. The contents of the presence of a marker indicating stable mutations is determined from the first set(s) of receptacles, and the sequence for the DNA or RNA fragments is determined from the second set(s) of receptacles. On the bases of these analyses, the genetic status of the genomic DNA or RNA material is determined. A system for performing such analyses is also disclosed.

22 Claims, 1 Drawing Sheet

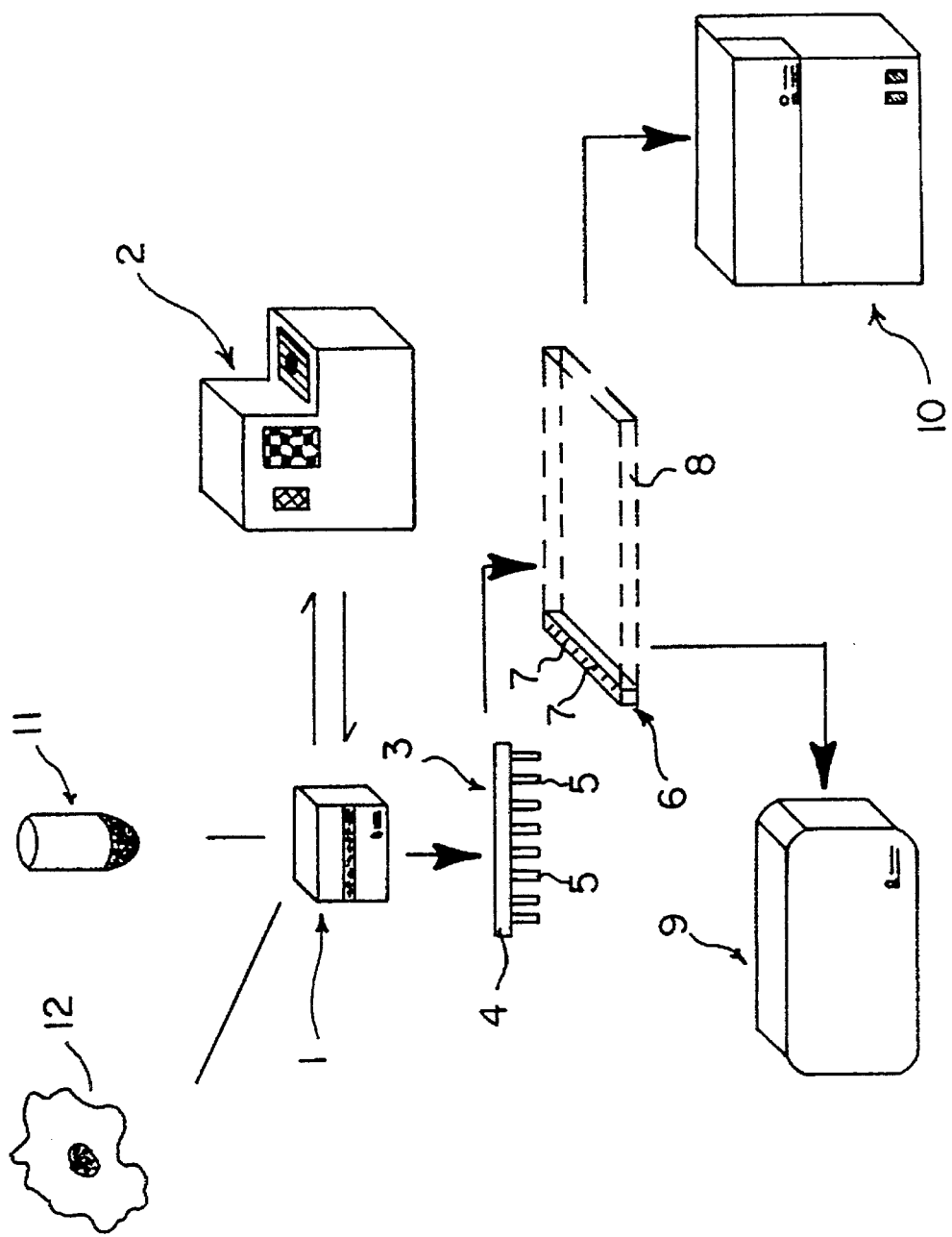

METHOD AND SYSTEM FOR MOLECULAR-BIOLOGICAL DIAGNOSTICS

FIELD OF THE INVENTION

The present invention relates to molecular-biological diagnostics, and more particularly to a novel method and system for analysing mutations or well-defined genetic events in coding DNA-sequences or corresponding RNA-sequences.

BACKGROUND OF THE INVENTION

The mammalian gene structure is based on coding DNA-sequences (exons) and intervening sequences (introns). Disturbances or changes (mutations) in the coding sequences result in abnormal gene products and thus malfunction and disease. Today, more than 4500 diseases are known which are due to defects in single genes. Such defects may be stable mutations, i.e. they always occur in specific, predictable positions, but may also be unstable genetic events occurring at one or more of a number of different unpredictable locations in the gene. In many cases the cause of a specific genetic disease may be stable or unstable events in any one of a number of exons. Detailed genetic information on an individual will tell about the susceptibility for disease, confirm inherited disorders, confirm disease status and serve as a guidance for more efficient treatment.

In the case of stable and thereby predictable mutations, methods permitting the determination of a specific polynucleotide sequence may be used, whereas the detection of unstable genetic events will require a DNA (or RNA) sequencing operation on the exon or exons in question. It is readily understood that with current methods, the determination of genetic diseases which may be due to one of several possible stable and unstable mutations will be laborious and time-consuming, requiring inter alia a great number of pipetting operations. The reproducibility will therefore be highly dependent on the skill of the operator. Besides, only a few commercial tests are available today for such genetic diseases, which tests, apart from being relatively complicated to perform, have a rather low accuracy.

Co-pending Swedish patent application 9203320-8 discloses a method of performing molecular-genetic reactions using a patrix-matrix type system, wherein the matrix part usually is a microtiter plate and the patrix part is a plate having a plurality of protrusions or extensions, each matching a respective well of the microtiter plate. The extensions are used as solid phase elements, each capable of binding a specific nucleic acid sequence from a solution and then keep it immobilized thereto for further processing or reaction by inserting the assembly of extensions into further microtiter wells. Such a system will permit a plurality of reactions to be performed simultaneously with reduced risk of contamination between reactions. While the use of the system for diagnostics tests is described in general, there is only a specific disclosure of the determination of stable mutations.

SUMMARY OF THE INVENTION

The present invention seeks to provide a novel method and system, respectively, for molecular-biological diagnostics, partially based upon the basic concept of the aforementioned Swedish patent application 9203320-8, which are devoid of the disadvantages of the prior art methods for molecular-biological diagnostics and which permit exon-specific determination of both stable and unstable mutations.

Thus, one object of the present invention is to provide an integrated assay format for the analysis of point mutations or well-defined genetic events in exons, i.e. coding DNA-sequences, or corresponding RNA sequences.

Another object is to provide a method and system for exon-specific testing which permit standardisation, high reproducibility and operator-adapted handling routines.

Still another object is to provide a method and system capable of providing all exon-specific testing with very high security (more than 95%) independently of the genetic disease, i.e. stable mutations as well as unstable genetic events.

A further object is to provide a method and system for exon-specific testing which basically are free of pipetting operations.

The above-mentioned objects are achieved with a method and system having the characteristics defined in the appended claims.

BRIEF DESCRIPTION OF THE DRAWINGS

The invention will now be described in more detail with reference to the accompanying drawing wherein the only figure, FIG. 1, is a schematic diagram showing a system for exon-specific genetic tests in accordance with the present invention.

DETAILED DESCRIPTION OF THE INVENTION

The system illustrated in the figure comprises a processing unit 1 for treating cells from blood (white blood cells) or tissue to obtain a genomic DNA or RNA preparation of a reproducible quality for direct amplification with any of the currently available genetical amplification methods. As an example of a suitable type of processing unit may be mentioned that described in WO 92/02303, in which an upper process microtiter type plate and a lower receiver plate are placed on top of each other, liquid being pressed from the upper plate to the lower plate by the application of gas pressure.

The illustrated system further comprises an amplification unit 2 for amplifying the exons, or more correctly, specific DNA or RNA fragments of interest to analyse with regard to the genetic defects in question (for the sake of simplicity referred to as exons herein). Such units are commercially available and need not be described further here. The specific DNA or RNA fragments may optionally be defined utilizing known intron specific sequences. In such a case the nucleic acid fragment in question will also comprise intron nucleotides at one or both ends.

A basic component of the system of the present invention is a pin member or strip 3 comprising a base portion 4 having a set of, in the illustrated case eight, extensions or pins 5 protruding therefrom in a comb-like fashion. The pins 5 support specific sequencing primers capable of binding to exons specifying a desired diagnosis. The necessary number of pins will depend on the specific exon to be analysed as will be discussed in more detail below. For a more detailed description of the pins 5 it may be referred to the aforementioned Swedish patent application 9203320-8.

The term "pin" is to be understood in a broad sense, meaning any kind of protrusion or extension fulfilling the intended purpose.

Preferably, the pin strips 3 are adapted to be assembled side-by-side to form, if desired, a strip assembly having two or more rows of pins 5 and thereby permit the simultaneous handling of a plurality of pin strips 3.

For each pin member, or strip, 3 there is a corresponding matching well member, or strip, 6 comprising a plurality of wells 7 corresponding to the pins 5 of the pin strip 3. Each genetic disorder requires a specific set of pins 5 and wells 7.

For exons containing stable and thereby predictable genetic changes, the wells 7 will contain all the reagents necessary for performing a complete analysis of a specific exon. The well strips 6 are preferably adapted to be assembled to a microtiter plate format 8 as indicated by the dashed lines in the figure.

For exons containing unstable and thereby unpredictable genetic changes, the wells 7 will contain the necessary components for a complete sequencing reaction, such as of the Sanger (dideoxy sequencing) type.

The reagents in the wells are preferably predispensed in dried form as is disclosed in, for example, EP-A-298 669. While the reagents may be in freeze-dried form, reagent mixtures dehydrated in the presence of a glass-forming substance to a glassified state are preferred, e.g. by using a sugar copolymer like Ficoll™, as described in U.S. Pat. No. 5,098,893, or trehalose, as described in U.S. Pat. No. 4,891, 319.

Finally, the system comprises detection means 9 and 10, respectively, for the detection of exons identified by the reactions using the pin and well strips 3 and 6, respectively.

For the detection, on one hand, of exons containing stable mutations, the detecting means 9 may be one that is capable of detecting incorporated markers, for example, as suggested in the figure, a conventional fluorometer or the like for measuring incorporated fluorescent markers.

For the detection, on the other hand, of exons which may contain unstable mutations, and optionally of exons which may contain several stable mutations, a sequencer 10 for determining the fine structure of the gene is included in the system. Such a sequencer is advantageously an automated DNA sequencer of the type which records signals generated in adjacent lanes as fluorescently labelled fragments move past a specified point in an electrophoretic sequencing gel. An example of such a sequencer is that described in U.S. Pat. No. 4,707,235 and commercialized as the "A.L.F. DNA Sequencer" by Pharmacia LKB Biotechnology AB, Uppsala, Sweden. This sequencer uses a single fluorescent label, a fixed laser beam, and fixed detectors spaced across the width of the sequencing gel.

The above described system may be used as follows for molecular-biological testing.

First, a genomic DNA or RNA preparation is prepared by lysing cells from blood 11 (white blood cells) or tissue 12 (obtained by biopsy or the like) and applied in specially designed preparation plates adapted for processing in processing unit 1. In the latter, the purification is effected by means of gel-slurries or, preferably, membranes in separation wells of the preparation plates as is per se known in the art. Thus, a preparation plate containing e.g. 24 patient samples is placed on top of a matching receiving plate in the processing unit 1, and the necessary liquids, such as lysing buffer and washing fluid, for the purification process are moved from one plate to the other by the application of air pressure, thereby accomplishing the desired purification. The result will be a genomic DNA or RNA preparation which may be directly used in any one of the commercially available amplification methods.

As an alternative, genomic DNA may be released from the cells by using the method disclosed in WO 91/08308, which comprises subjecting the cells to a temperature of at least 105° C. for a time period of at least 5 minutes. The resulting DNA preparation, containing single-stranded DNA, may be directly used in an amplification process without further purification.

While it may, at least in some cases, be possible to subject the obtained genomic DNA or RNA preparation to a defined cleavage procedure to produce the specific fragments which are to be subsequently analysed with respect to the genetic defects tested for, it is in most cases preferable to produce these specific DNA or RNA fragments by amplification in amplification unit 2. As mentioned above, the specific DNA or RNA fragments may be defined by known intron specific sequences, in which case the fragments will in addition to the exon nucleotides also contain intron nucleotides.

Amplification may be based upon any one of the amplification methods which are commercially available, such as polymerase chain reaction (PCR), nucleic acid sequence-based amplification (NASBA), or self-sustained sequence replication (3SR). The amplification is performed in per se known manner in a number of amplification tubes to which different primers are added to amplify the desired DNA fragments. After completed amplification (usually 20–30 cycles), a selected sample material has been obtained which contains defined DNA or RNA fragments in a sufficient amount for permitting the application of a detection method defining exon-specific genetic changes in detail as will described below.

For simplifying the performance of the amplification procedure, the necessary amplification reagents, such as primers, nucleotides, enzyme and buffer, may be added stabilised on one end of a plastic strip (for example, of the conventional type used for the detection of sugar in urine).

In the next step, the specific reactions required for detecting the exon-specific genetic changes tested for with high reproducibility are performed. This is effected using the pin strip 3 described above which permits pipetting-free handling. Thus, a set of pin strips 3 and well strips 6 specific for a selected genetic disease is provided. As an example, suppose that the genetic disease in question may be due to any one of unstable (and thereby unpredictable) changes in one exon, and stable point mutations in, say, two exons. In this case, two pin strips 3 may be used, one for detecting the stable mutations and one for detecting the unstable mutations. In both cases the individual pins 5 of the pin strip 3 will support exon-specific primers capable of binding to selected exons. Thereby these exons may be fished from the amplified genomic DNA or RNA preparation by introducing the pins 3 into the corresponding amplification tubes.

The necessary number of pins 5 on the pin strip 3 for detecting a stable mutation in an exon will depend on the particular method selected for the detection. Generally, one or two pins 5 per exon will suffice, in many cases only one. However, especially for stable mutations, but also for unstable mutations, it is, in fact, also possible to use one pin for several exons as will be further discussed below.

As an example, the illustrated pin strip 3 which contains eight pins 5 may be prepared to either bind up to eight different exons, or one exon from up to eight different patient samples. In the assumed case of two stable mutations, one pin strip 3 may thus, if desired, be used for testing four different patient samples simultaneously.

The desired detection reactions are then started by dipping the pins 5, having the respective exon or exons bound thereto, into the corresponding wells 7 in well strip 6, which wells contain the necessary reagents predispensed and stabilised.

For detecting stable mutations, several different methods may be used, comprising the incorporation of a detectable marker, e.g. a fluorophore or chromophore. One such method is described in WO 90/09455 and comprises the steps of (i) treating the pin bound exon with an oligonucleotide primer complementary to a portion thereof containing the mutation, extending the bound primer such that the extended product includes a detection element and separation element, separating the extended product into a fraction free of any detectable element which has not been incorporated into the extended product, and assaying this fraction for the detectable element (such as a fluorescent marker), the presence of which indicates presence of the mutation in the exon. This method may be characterized as a mini-sequencing method.

Another method is the oligonucleotide ligation assay (OLA) described in U.S. Pat. No. 4,998,617. In this method the possibility of covalently binding two oligonucleotide probes selected to anneal to immediately adjacent segments is studied, one of the segments having the possible mutation at the linking end. One of the probes has a separation element and the other a detectable element (such as a fluorescent marker). Correct base-pairing is necessary for covalent binding, and if only the mutation will permit correct base-pairing, the presence of the marker in a separated segment is indicative of the mutation.

It is understood that the above methods for detecting stable mutations will permit the use of one and the same pin for several exons. Thus, the pin may support, say, up to five different exons if a corresponding number of markers is used, e.g. five different chromophores. The possible number of exons per strip is therefore dependent on the number of different distinguishable markers available.

In the case of unstable changes, a complete sequencing of the exon in question will be necessary. In case both the DNA strands are to be sequenced, all eight pins 5 have to be used for the same exon, one pin per nucleotide and strand. It may, however, be sufficient to sequence only one strand, and in such a case four pins will be required per exon. This means that two exons may be tested with each pin strip, or alternatively the same exon from two patient samples. However, in the same way as mentioned above for stable mutations, it may also be possible to use one pin for two or more exons, utilizing several different markers.

Of course, sequencing of the exon may also be preferable in the case of an exon containing several stable mutations, as already mentioned above.

Sequencing reactions according to Sanger (dideoxy sequencing), for example, may be performed in per se known manner by dipping the pins into the wells of a corresponding well strip, the wells containing the necessary predispensed reagents (e.g. T7 DNA polymerase, nucleotides, nucleotide analogs, buffer).

If desired, two or more pin strips 3 may be assembled as described above, as may also the corresponding well strips 6. Hereby a test for several exons may be performed simultaneously and/or several patient samples be tested simultaneously.

The final detection of the exons identified by the reactions effected above is then performed.

In the case of stable mutations, the corresponding reaction mixtures in the wells 7 of the respective well strip 6 may be analysed by conventional manner in the fluorometer 9. In the case of the described mini-sequencing method, the result will be a quantification of the different bases incorporated into the sample. Since the incorporation is sequence-specific, it may thus easily be determined whether the patient is homozygous or heterozygous with respect to any one of the detected changes.

In the case of unstable mutations, on the other hand, the reaction contents of the wells 7 of the corresponding well strip(s) 3 are applied to the sequencer 10 for determining the DNA or RNA sequence of the exon. The result will thus be a determination of the fine structure of the exon, thereby permitting the details of complex genetic changes to be detected with great accuracy.

The final diagnosis will be obtained from the combined results of the two types of analyses performed.

A more detailed example of the performance of a test in accordance with the above procedures will now be described.

EXAMPLE

Purification of Genomic DNA

1. Apply <1 ml of blood into the well (on the membrane) of a preparation plate in the processing unit 1.
2. Close the lid of the unit and press the liquid through the membrane, the blood cells remaining on the latter.
3. Add ≈3 ml of wash buffer per well and press the liquid through the membrane. This step will wash away the red blood cells and leave the white cells on the membrane.
4. Add ≈1 ml of lysing buffer and incubate at room temperature.
5. Close the lid and press the liquid through the membrane. The genomic DNA preparation will now remain on the membrane.
6. Add 1–3 ml of wash buffer and press through the membrane.
7. Dissolve the DNA in a minimum amount of water.
8. Transfer 1 reaction volume to amplification tubes for processing in amplification unit 2.

Amplification

1. Add amplification reagent either as a stabilised totally integrated format (e.g. a dip stick having the reagents on one end) or as part components.
2. Incubate corresponding to 20–30 reaction cycles.

Reaction Chemistry a) Stable Mutations
1. Add 20 µl of water to all wells 7 to be used.
2. Dip the exon-specific pin strip 3 into the amplification tubes as obtained after the amplification step and incubate for 5 minutes (annealing).
3. Lift up the pin strip 3 and dip it into a wash bath, wait for 10 seconds and then remove.
4. Shake off excess liquid with a quick shaking movement.
5. Dip the washed pin strip 3 into the reaction-specific well strip 6.
6. Incubate 5–10 minutes at room temperature (extension).
7. Repeat steps 3 and 4.
8. Measure the fluorescence in fluorometer 9.

b) Unstable Mutations
1. Add 20 µl of water to all wells 7 to be used.
2. Pipette the amplification reaction into 4 tubes in 4 equal volumes (≈20 µl).

3. Dip the exon-specific pin strip 3 into the amplification tubes as obtained after the amplification step and incubate for 5 minutes (annealing).
4. Lift up the pin strip 3 and dip it into a wash bath, wait for 10 seconds and then remove.
5. Shake off excess liquid with a quick shaking movement.
6. Dip the washed pin strip 3 into the reaction-specific well strip 6.
7. Incubate 5–10 minutes at room temperature (extension).
8. Repeat steps 4 and 5.
9. Transfer to stop solution and denature.
10. Apply to DNA sequencer and detect sequence.

The present invention is, of course, not restricted to the embodiments specifically described above and shown in the drawing, but many modifications and changes obvious to the skilled person may be made without departing from the scope of the inventive concept as defined in the following claims. The disclosure of all the patent applications and patents referred to hereinbefore is incorporated by reference herein.

I claim:

1. A method for testing genomic DNA or RNA for the presence of mutations, comprising the steps of:
   a) providing a genomic DNA or RNA preparation;
   b) processing said genomic DNA or RNA preparation to produce a processed preparation which contains desired DNA or RNA fragments to be tested for the presence of mutations;
   c) contacting at least one first set of interconnected pins, each pin supporting an oligonucleotide primer capable of hybridizing with a specific DNA or RNA fragment, with said processed DNA or RNA preparation to bind a defined DNA or RNA fragment to be tested for the presence of a stable mutation to each pin, and/or
   d) contacting at least one second set of interconnected pins, each pin supporting an oligonucleotide primer capable of hybridizing with a specific DNA or RNA fragment, with said processed DNA or RNA preparation to bind a defined DNA or RNA fragment to be tested for the presence of an unstable mutation, or several stable mutations to each pin;
   e) introducing the pins of said first set into a matching first set of interconnected receptacles containing reaction mixtures for producing in each receptacle reaction products which reaction products, when there is a mutation in the supported DNA or RNA fragment, contain a marker incorporated therein because of the mutation, and/or
   f) introducing the pins of said second set into a matching second set of interconnected receptacles containing reaction mixtures for performing sequencing reactions in said receptacles;
   g) analysing the contents of said first set of receptacles to determine the presence of said marker indicating a stable mutation, and/or
   h) analysing the contents of said second set of receptacles to determine the sequence of the DNA or RNA fragments; and
   i) determining on the basis of the results of the analyses in steps g) and/or h) the genetic status of said genomic DNA or RNA material.

2. A method according to claim 1, wherein at least one pin in said first set is used for each DNA or RNA fragment to be tested for the presence of a stable mutation.

3. A method according to claim 1, wherein four or eight pins in said second set are used for each DNA or RNA fragment to be tested for the presence of an unstable mutation or several stable mutations.

4. A method according to claim 1, wherein one pin is used for two or more specific DNA or RNA fragments to be tested for the presence of stable mutations, and/or one pin is used for two or more specific DNA or RNA fragments to be tested for the presence of unstable mutations.

5. A method according to any one of claims 1 to 4, wherein the number of pins and the number of receptacles in said first sets each is eight.

6. A method according to any one of claims 1 to 4, wherein the number of pins and the number of receptacles in said second sets each is eight.

7. A method according to any one of claims 1 to 4, wherein step b) comprises an amplification reaction.

8. A method according to claim 1 wherein step e) comprises
   i) treating the solid phase bound DNA or RNA with an oligonucleotide primer complementary to a portion thereof containing a mutation,
   ii) extending bound primer such that an extended product is generated which includes a detection element and separation element, and
   iii) separating said extended product into a fraction free of any detectable element which has not been incorporated.

9. A method according to claim 1 wherein step e) comprises an oligonucleotide ligation assay.

10. A method according to claim 1 wherein step g) comprises detection of a fluorescent marker or a chromophoric marker.

11. A method according to claim 1 wherein step h) comprises analyzing the contents of said second set of receptacles with an automated sequencer.

12. A system for testing genomic DNA or RNA for the presence of mutations, comprising:
   (i) at least one first set of interconnected pins, each solid phase member supporting an oligonucleotide primer capable of hybridizing with a specific sample DNA or RNA fragment to be tested for the presence of a stable mutation, and
   (ii) at least one first set of interconnected receptacles matching said at least one first set of pins and containing predispensed dried reaction mixtures capable of producing reaction products containing an incorporated marker in the presence of a DNA or RNA fragment containing a defined stable mutation; and/or
   (iii) at least one second set of interconnected pins, each pin supporting an oligonucleotide primer capable of hybridizing with a specific sample DNA or RNA fragment to be tested for the presence of an unstable mutation or several stable mutations, and
   (iv) at least one second set of interconnected receptacles matching said at least one second set of pins and containing predispensed dried reaction mixtures capable of a sequencing reaction in the presence of a DNA or RNA fragment.

13. A system according to claim 12, which comprises said first and second set of interconnected pins and wherein said first and second sets of interconnected pins and interconnected receptacles each contain a row of eight pins and receptacles, respectively.

14. A system according to claim 12 or 13, wherein said first set of pins comprises at least one pin for each specific DNA or RNA fragment to be tested for the presence of a stable mutation.

15. A system according to claim 12, wherein said second set of pins comprises four or eight pins for each specific DNA or RNA fragment to be tested for the presence of an unstable mutation or several stable mutations.

16. A system according to claim 12, wherein said first set of pins comprises single pins for two or more specific DNA or RNA fragments to be tested for the presence of stable mutations, and/or said second set of pins comprises single pins for two or more specific DNA or RNA fragments to be tested for the presence of an unstable mutation or several stable mutations.

17. A system according to claim 12, wherein said first and second sets of interconnected pins are adapted to be put together to assemblies of two or more first and/or second sets.

18. A system according to claim 12, wherein said first and second sets of interconnected receptacles are adapted to be put together to assemblies of two or more first and/or second sets.

19. A system according to claim 12, wherein said first and second sets of interconnected pins each comprise pins supported by a strip member.

20. A system according to claim 12, wherein said first and second sets of interconnected receptacles each comprises microtiter type wells in a well member.

21. A system according to claim 12, which further comprises fluorophore or chromophore detecting means and DNA or RNA sequencing means.

22. A system according to claim 21, which further comprises DNA or RNA amplification means.

* * * * *